(12) United States Patent
Roessler

(10) Patent No.: US 10,772,537 B2
(45) Date of Patent: Sep. 15, 2020

(54) METHOD AND SYSTEM FOR DETERMINATION OF PHYSIOLOGICAL ACTIVITY SIGNALS

(71) Applicant: Siemens Healthcare GmbH, Erlangen (DE)

(72) Inventor: Juergen Roessler, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 958 days.

(21) Appl. No.: 15/366,644

(22) Filed: Dec. 1, 2016

(65) Prior Publication Data
US 2017/0150906 A1 Jun. 1, 2017

(30) Foreign Application Priority Data
Dec. 1, 2015 (DE) .................. 10 2015 223 946

(51) Int. Cl.
*A61B 5/11* (2006.01)
*A61B 5/00* (2006.01)
(Continued)

(52) U.S. Cl.
CPC .......... *A61B 5/1118* (2013.01); *A61B 5/0033* (2013.01); *A61B 5/0205* (2013.01); *A61B 5/0507* (2013.01); *A61B 5/1102* (2013.01); *A61B 5/113* (2013.01); *A61B 5/1135* (2013.01); *A61B 5/7292* (2013.01); *A61B 6/032* (2013.01); *A61B 6/527* (2013.01); *A61B 6/0407* (2013.01); *A61B 2562/046* (2013.01)

(58) Field of Classification Search
CPC ..... A61B 5/0205; A61B 5/0507; A61B 5/113; A61B 5/1118
See application file for complete search history.

(56) References Cited

U.S. PATENT DOCUMENTS 5,827,195 A * 10/1998 Lander ................ A61B 5/0452
600/509
2007/0118054 A1 * 5/2007 Pinhas ................. A61B 5/4812
600/587
(Continued)

OTHER PUBLICATIONS

Pfanner, et al., "Monitoring respiratory and cardiac motion in CT using a continuous wave Doppler radar," European Society of Radiology, pp. 1-12 (2013).
(Continued)

*Primary Examiner* — Jeffrey G Hoekstra
*Assistant Examiner* — Jason M Ip
(74) *Attorney, Agent, or Firm* — Schiff Hardin LLP

(57) ABSTRACT

In a method and apparatus for determining a physiological activity signal in a subject using various movement sensors that each transmit a temporal movement signal, a physiological reference signal is determined from the various movement signals that best depicts a physiological movement of the subject, the movement sensor that generates the physiological reference signal is identified as a physiological reference sensor, at least one physiological addition signal is determined from the temporal movement signals that is similar to the physiological reference signal up to a limit, and the physiological reference signal and the at least one addition signal are added to form the physiological activity signal.

24 Claims, 5 Drawing Sheets

(51) Int. Cl.
*A61B 5/113* (2006.01)
*A61B 5/05* (2006.01)
*A61B 6/00* (2006.01)
*A61B 5/0205* (2006.01)
*A61B 6/03* (2006.01)
*A61B 6/04* (2006.01)

(56) References Cited

U.S. PATENT DOCUMENTS

2009/0192384 A1 7/2009 Fontius
2010/0292559 A1 11/2010 Hannemann et al.

OTHER PUBLICATIONS

Fletcher, et al., "Wearable Doppler Radar with Integrated Antenna for Patient Vital Sign Monitoring," Institute of Electrical and Electronics Engineers, pp. 276-279 (2010).

Jang, et al., "Wireless Bio-Radar Sensor for Heartbeat and Respiration Detection," Progress in Electromagnetics Research C, vol. 5, pp. 149-168 (2008).

Scalise, "Non Contact Heart Monitoring, Advances in Electrocardiograms," Methods and Analysis (PhD. Richard Millis (Ed.)), ISBN: 978-953-307-923-3, InTech, www.intechopen.com/books/advances-in-electrocardiograms-methods-and-analysis/non-contact-heartmonitoring, pp. 81-108 (2012).

Thijs, et al., "A Comparison of Continuous Wave Doppler Radar to Impedance Cardiography for Analysis of Mechanical Heart Activity," Proceedings of the 2005 IEEE, Engineering in Medicine and Biology 27th Annual Conference, pp. 3482-3485 (2005).

Varanini, et al., "Cardiac and Respiratory Monitoring through Non-Invasive and Contactless Radar Technique," Computers in Cardiology, vol. 35, pp. 149-152 (2008).

Obeid, et al., "Microwave Doppler Radar for Heart Beat Detection Versus Electrocardiogram: A Validation Approach," hal.archives-ouvertes.fr/hal-00873944 (2013).

* cited by examiner

METHOD AND SYSTEM FOR DETERMINATION OF PHYSIOLOGICAL ACTIVITY SIGNALS

BACKGROUND OF THE INVENTION

Field of the Invention

The present invention concerns a method for determining a physiological activity signal in a subject using a system having several movement sensors. The invention further relates to the associated system for determining the physiological activity signal and a storage medium encoded with programming instructions for implementing such a method.

Description of the Prior Art

Knowledge of respiratory activity and heartbeat activity are of fundamental importance for imaging such as for an MR system or CT system, in order to be able to prevent motion artifacts because then recording of the measurement data in the MR or CT system can be synchronized with the heartbeat activity or respiratory movement by triggering. Heartbeat activity is usually measured by means of EKG detection, but this is time-consuming, because each EKG electrode has to be attached to the ribcage. Furthermore, methods for the detection of heartbeat and respiration with the use of radar sensors are known, as described in exemplary fashion in the following publications:
1. "Monitoring respiratory and cardiac motion in CT using a continuous wave Doppler radar" (F. Pfanner, T. Allmendinger, T. Flohr, M. Kachelrieβ)
2. "Cardiac and Respiratory Monitoring through Non-Invasive and Contactless Radar Technique" (M Varanini, P C Berardi, F Conforti, M Micalizzi, D Neglia, A Macerata)
3. "Radar monitoring of heartbeats and respiration" (Øyvind Aardal)
4. WIRELESS BIO-RADAR SENSOR FOR HEARTBEAT AND RESPIRATION DETECTION" (B.-J. Jang, S.-H. Wi and J.-G. Yook, M.-Q. Lee, K.-J. Lee)

Furthermore, methods are known which detect the heartbeat (or EKG) with the aid of radar sensors:
5. Microwave Doppler Radar for Heart Beat Detection Versus Electrocardiogram: A Validation Approach (Dany Obeid, Sawsan Sadek, Gheorghe Zaharia, Ghais El Zein)
6. Non Contact Heart Monitoring (Lorenzo Scalise)
7. Wearable Doppler Radar with Integrated Antenna for Patient Vital Sign Monitoring (Richard Ribón Fletcher, Sarang Kulkarni)
8. A Comparison of Continuous Wave Doppler Radar to Impedance Cardiography for Analysis of Mechanical Cardiac activity (J. A J. Thijs, J. Muehlsteff, O. Such, R. Pinter, R. Elfring, C. H. Igney)

FIG. 1 shows a diagrammatic view of how several transmitting and receiving antennas can be used, which have a fixed spatial arrangement. This system of the prior art has a radar unit 10 with several transmitting antennas 11-14 and a receiving antenna 15. Likewise it is conceivable that the antennas are alternately transmitting and receiving antennas. Problematic with all these devices and methods is that respiratory signals and signals from heartbeat activity overlap and can only be separated with difficulty. This is because radar sensors detect movements and represent these movements as signals. As heartbeat and respiratory movement occur simultaneously, both activities also overlap in the resulting radar signal. When it is an uninterrupted respiratory signal that is of interest, the heartbeat activity that is additionally visible in the signal may be disturbing. Likewise, when it is the heartbeat signal that is of interest, the respiratory movement additionally visible in the signal can be disturbing. Both signals, heartbeat and respiratory movement, are therefore each available only in a disturbed fashion as a result of known radar arrangements. However, this means that use as a trigger signal for heartbeat activity or respiratory activity is barely or only imperfectly possible, leading to a deterioration in image quality. Furthermore, a disadvantage of radar arrangements according to the prior art is that due to their fixed position, they are not optimally positioned for all subjects, from large adults to children, from slim to fat patients, with the consequence that the quality of the signals generated fluctuates greatly depending on the patient being examined.

SUMMARY OF THE INVENTION

An object of the present invention is to avoid the aforementioned disadvantages and to provide a method and a system in which, regardless of the person examined, physiological activities such as cardiac movement or respiratory movement can be clearly identified.

According to a first aspect of the invention, a method for determining a physiological activity signal in a subject is implemented with the use of a system that has several movement sensors, which each transmit a temporal movement signal. The sensor that provides the best signal, i.e. for example best detects respiratory movement or cardiac movement, can be identified among the various movement sensors and the associated movement signals. If further signals are subsequently identified from the movement signals—the addition signals—which match the reference signal up to a limit or threshold value, a good activity signal can be obtained through the addition of the reference signal and the addition signals and can be used, for example, to trigger images in an imaging device such as a CT system or an MR system.

The various movement sensors are preferably several radar sensors that can be installed in a couch of a medical imaging device.

The physiological activity signal may contain a respiratory movement of the subject, in which case the physiological reference signal is a respiratory reference signal which is detected by a respiratory reference sensor. The physiological addition signal then contains a respiratory addition signal, and the respiratory reference signal and the respiratory addition signal are added to form a respiratory activity signal.

Furthermore, the physiological activity signal may contain a cardiac movement of the subject, in which case the physiological reference signal is a cardiac reference signal which is detected by a cardiac reference sensor. The physiological addition signal may contain a cardiac addition signal, and the cardiac reference signal and the cardiac addition signal may be added to form a cardiac activity signal.

The system can also detect both physiological signals simultaneously and generate both a respiratory activity signal and a cardiac activity signal. In doing so, it is possible, for example, that the movement sensors that generate neither the respiratory reference signal, nor the at least one respiratory addition signal, nor the cardiac reference signal, nor the cardiac addition signal, are deactivated. If only one of the two activity signals is to be detected, all sensors that do not detect the associated reference signal or addition signal can be deactivated. The movement sensors such as the radar sensors can all be controlled simultaneously so that they all transmit and receive simultaneously. However, it is also possible for all the radar sensors in a cycle to be only briefly activated so that only one radar sensor is ever active at any one time. It is also conceivable to activate, at any one time, only the radar sensors that are far enough away from each other geometrically to enable mutual interferences and disturbances to be largely avoided. However, radar sensors that cannot be assigned to any of the groups of sensors that detect respiratory activity or cardiac activity can be deactivated.

To determine the respiratory reference signal or the cardiac reference signal, in each case it is possible to detect the signal with the greatest amplitude in a respiratory rate range or a cardiac rate range among the movement signals and in each case to use the signal with the greatest amplitude as the respiratory reference signal or the cardiac reference signal. The determination of the signal with the greatest amplitude can preferably take place in the respective frequency range in the respiratory rate range or cardiac rate range.

Because the detected signals usually contain signals from both movement components, filtering is provided. For example, the temporal movement signals can be filtered with a first filter to generate respiratory movement signals in which the signal components induced by a cardiac movement are suppressed compared to signal components induced by a respiratory movement, wherein the respiratory reference signal is determined from the respiratory movement signals.

Usually, respiratory rates are between 10 per minute and 30 per minute, i.e. between 0.16 Hz and 0.5 Hz. Thus, the heart signal components can be filtered out as the cardiac rate is usually between 35 per minute to 200 per minute, i.e. in a frequency range of 0.58 Hz to 3.33 Hz. To identify cardiac movement signals, the movement signals can be filtered using a second filter. The cardiac reference signal can then be determined from the cardiac movement signal components.

In determining the cardiac addition signal or the respiratory addition signal, the signals from the other sensors which are similar to the respective reference signal are reviewed. This can be done with the use of a cross-correlation function or a cross-covariance function.

The various movement sensors can be divided into at least two separate subgroups, wherein the respective subgroup in which the cardiac reference sensor and the respiratory reference sensor are arranged is identified. If the two reference sensors are in the same subgroup, the movement sensors of the at least one other subgroup can be deactivated. As it is possible that the subject is moved into the imaging device feet-first or head-first and in a face-down or supine position, the movement sensors like the radar sensors should cover a large spatial area. This can take place by arranging various sensors in physically separated subsections. If the cardiac reference sensor and the respiratory reference sensor are now in the same subsection, then it is unlikely that meaningful signals are still detected in another subsection which is then covered, for example, by the feet, enabling these sensors to be deactivated.

Likewise, it is possible that a position of the respiratory reference sensor within the various movement sensors is determined or the position of the cardiac reference sensor. To determine the addition signals which are combined with the respective reference signal, movement sensors can then preferably be considered which are immediately adjacent to the respective reference sensor, as it highly probable that the sensors adjacent to the reference sensors also provide relatively good signals, while sensors which are very far away from the respective reference sensor can probably contribute little to the addition signals.

The invention also encompasses the associated system with the various movement sensors and an evaluation computer that evaluates the various signals as described above.

The invention also encompasses an electronically readable data storage medium encoded with programming instructions that, when the storage medium is loaded into a computer, causes the computer to implement the method according to the invention when the programming instructions are executed by the computer.

DESCRIPTION OF THE PREFERRED EMBODIMENTS

Figure 1:
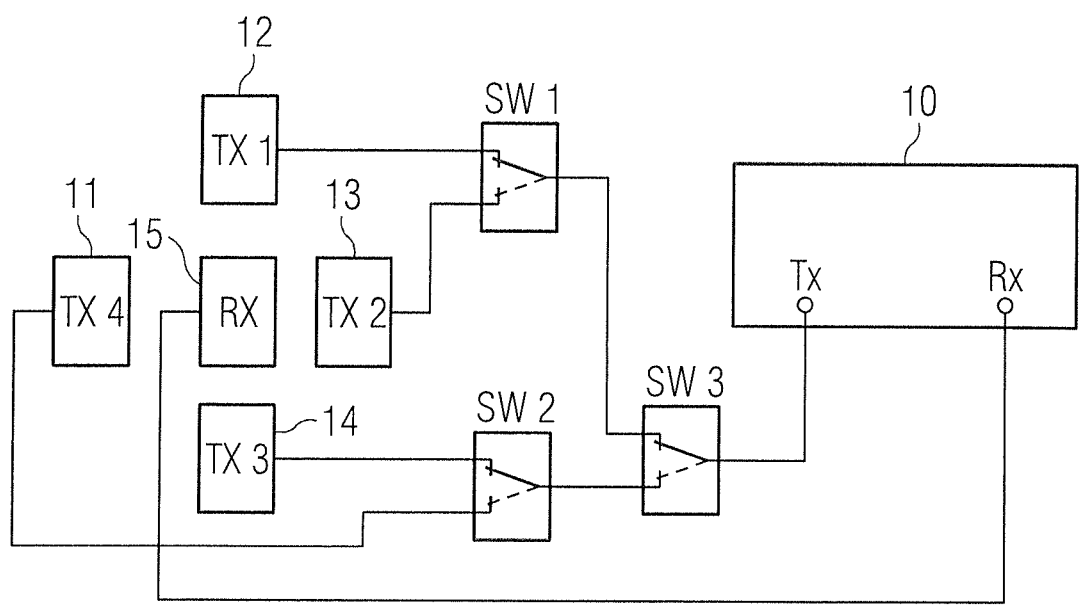
FIG. 1 shows a sensor arrangement for detecting respiratory and cardiac movements according to the prior art.
Figure 2:
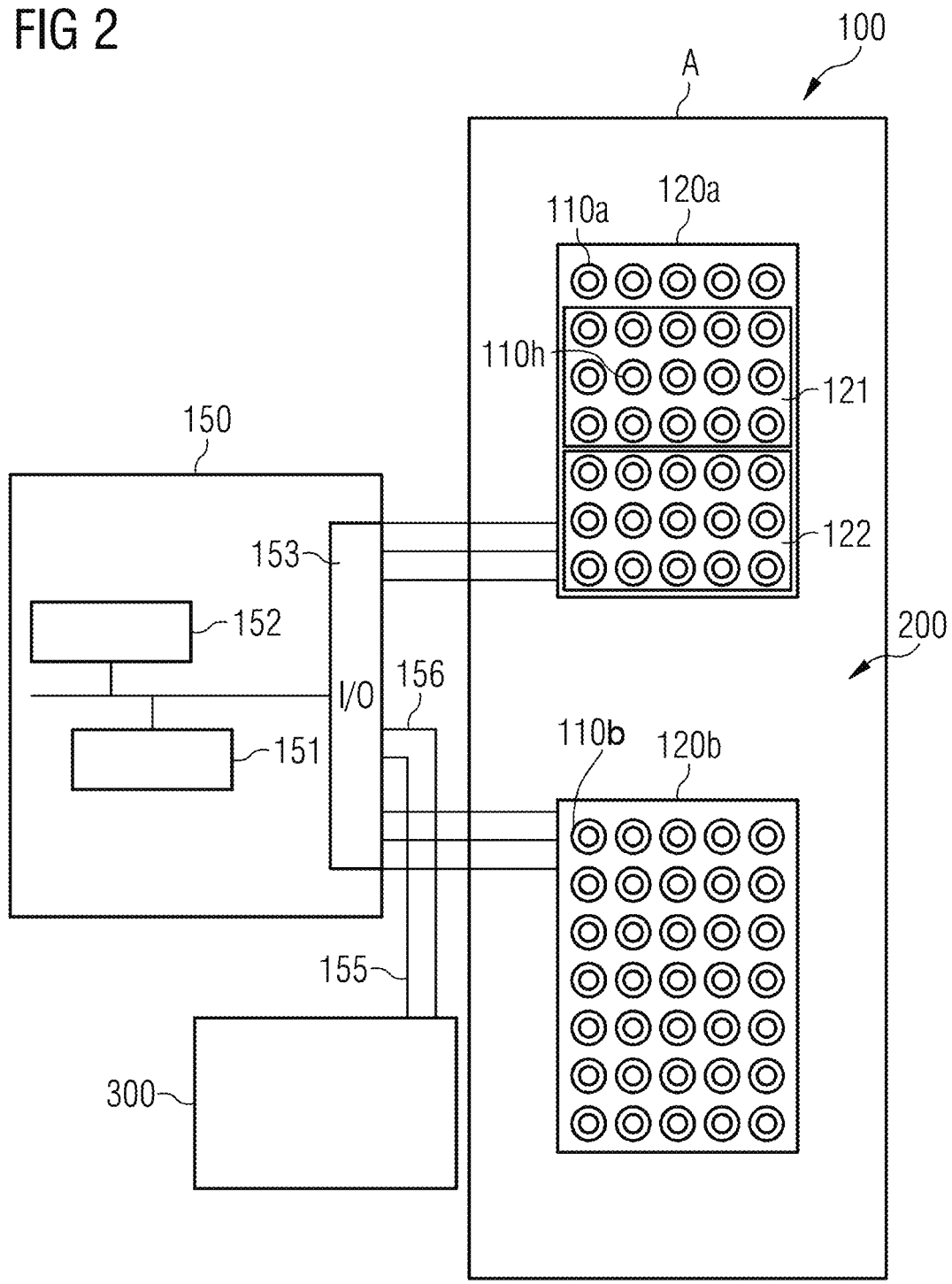
FIG. 2 shows a system with which cardiac activity and/or respiratory activity can be inventively identified.

A system or a method is described with which a respiratory signal or a signal of the cardiac activity is robustly identifiable. FIG. 2 shows such a system 100, which can be implemented in a patient couch 200. The system has a multiplicity of radar sensors 110a and 110b which in the example shown are arranged in two different subsections 120a and 120b. Both the subgroups of the radar sensors 110 in the subsections 120a and 120b are physically separated from each other. Both subsections can, for example, be 50 cm long and 40 cm wide but other proportions are also conceivable. Altogether, the two subsections are dimensioned such that a respiratory signal or a cardiac signal can be detected in a subject who can be moved into an imaging device 300 (shown only in a diagrammatic view) either feet-first, i.e. with the feet in the direction of the edge A, or head-first. The couch 100 may be part of the imaging device. The imaging device 300 may be an MR system or CT system of a known type. As the subject can either be moved into the imaging device 300 in a supine position or face-down, the subsections 120a and 120b must be designed such that the cardiac movement can be detected in both a face-down and a supine position. The ribcage of the subject can therefore be located either in the subsection 120a or in the subsection 120b. The two subsections 120a and 120b are preferably arranged symmetrically to one another so that a face-down and a supine position or a position in which the subject is moved feet-first or head-first into the imaging device can be covered. However, more than two subsections 120a and 120b can also be provided. Each subsection 120a, 120b can in turn be divided into three subsections, each with a subsection for the detection of respiration and two subsections for the detection of cardiac activity depending on a face-down or supine position. Radar sensors can be used as sensors; alternatively coils can also be used that are designed such that bodies in the vicinity of the coils generate another magnetic field in the coils. When using radar sensors, in principle they can all be controlled simultaneously so that they all transmit and receive simultaneously. However, care should be taken so that the radar signals transmitted by one radar sensor are not received by another radar sensor. It is therefore conceivable for all radar sensors in a very fast cycle to each be activated only briefly, so that at any one time only one radar sensor is ever briefly active. Furthermore, it is possible that, at any one time, only radar sensors are activated that are far enough away from each other so as to geometrically exclude mutual disturbances. At any one time, therefore, only one subgroup is active. This active subgroup can be, for example, a group of sensors in the subsection 120a, and another group of sensors in the subsection 120b, or various groups in a subsection that are far enough away from each other for a radar sensor of one subgroup not to receive the reflection signal that has been sent by a radar sensor of another subgroup. All the radar sensors can be briefly active in succession until the sequence recommences. In doing so, depending on the position of the subject, the radar sensors are now dynamically assigned to a group for the detection of respiration or to a group for the detection of cardiac activity, wherein the sensors which are not assigned to either of the two groups can be deactivated.

As described in detail below, the signals of the individual groups are each added to generate a cardiac activity signal 155 or a respiratory activity signal 156 which can be supplied by an evaluation unit 150, subsequently described in more detail, to an imaging device 300.

How the cardiac activity signal or the respiratory activity signal can be generated and how the respiratory and cardiac signals can be separated is explained below with reference to FIGS. 3 and 4.

In a learning phase, as noted above the various radar sensors can be individually controlled, either in succession or simultaneously, depending on the respective spacing of the sensors. In connection with FIG. 3, the determination of a cardiac activity signal is explained with the use of the movement signals that are detected by the radar sensors 110a and 110b. The movement signals are detected in step S30. Then the signals can be filtered with a high pass filter or band pass filter to pass all the signal components in the typical cardiac rate range of 35 per minute to 200 per minute, i.e. between approx. 0.58 Hz and 3.3 Hz. As a result of this filtering, cardiac movement signals that essentially contain the signal components on the basis of the cardiac movement are thus generated in step S31. Then the radar signal that detects the cardiac activity with the highest amplitude is determined from the filtered signals. This determination can take place in the time range of the signal, as well as in the frequency range, wherein the highest peak or the highest amplitude in the frequency range is decisive. This corresponds to the step S32 of FIG. 3 of the determination of the cardiac reference signal. With reference to FIG. 2, this may be the sensor with the reference character 110h, for example. In the presence of a total of N movement sensors, all the additional N−1 sensors can then be assessed with regard to the similarity of the signals to the reference signal of the reference sensor 110h. This can be done, for example, with the use of a cross-correlation, wherein all the signals filtered in the cardiac rate range can be assessed for similarity, or only signals from sensors in the vicinity which are at a predetermined distance from the reference sensor. In the example shown in FIG. 2, it may be useful, for example, not to take the sensors of the subsection 120b into consideration if the cardiac reference sensor 110h is located in the subsection 120a. The cross-correlation function is as follows:

$$R_{XY}(k)=\Sigma_{n=-\infty}^{\infty}x(n)\cdot y(n+k) \qquad (1)$$

The cross-correlation function $R_{XY}$ describes the similarity between two temporal signals, namely the signals X and Y, as a function of the time n. This determination of the cardiac addition signals takes place in step S33 with reference to FIG. 3. In this step S33, all the signals which have an adequate relationship to the cardiac reference signal are taken into consideration, adequate here meaning similar up to a limit or threshold value. This limit or threshold value may also be selected and altered by a user of the system of FIG. 2 as a function of the quality of the respective signals. Thus only signals with adequate similarity are taken into consideration, so that signals with a poor signal-to-noise ratio are not taken into consideration. Then the cardiac reference signal can be added to the cardiac addition signals to form the cardiac activity signal, as shown in step S34 of FIG. 3.

Similarly, the respiratory activity signal can be generated, as explained below with reference to FIG. 4. The movement signals detected by the sensors 110a, 110b are recorded (S40). Then the signals are filtered with a low pass filter or band pass filter to pass all the signal components in the typical respiratory frequency range between 0.16 Hz and 0.5 Hz, or to suppress the other signal or frequency components. This is with reference to step S41 in FIG. 4: determination of the respiratory movement signal for the individual sensors. In a step S42 the respiratory reference signal is then determined, wherein in turn either in the time or frequency range the highest amplitude in the time or frequency range which forms the respiratory reference signal is established. In step S43, the respiratory addition signals that are sufficiently similar to the respiratory reference signal are then determined. All N−1 signals of the radar sensors filtered in the respiratory frequency range can in turn be correlated with the signal of the respiratory reference sensor filtered in the respiratory frequency range using the above equation (1) where K=0. The signals that have a greater similarity than a limit or threshold value can then be used as respiratory addition signals to obtain the activity signal in step S44.

Instead of cross-correlation, another cross-covariance function can be used as shown below in equation (2).

$$G_{XY}(k)=\Sigma_{n=-\infty}^{\infty}[x(n)-\mu_X]\cdot[y(n+k)-\mu_Y] \qquad (2)$$

With the cross-covariance function, mean-adjusted signals are used, wherein the mean-adjusted signals are totaled to determine the respective activity signal. Altogether, for equation (1) and (2) only a finite number of samples is added to determine the cross-correlation or cross-covariance function.

In another embodiment, not only K=0 is used for the evaluation of the equation as a number, but a range which, for example, corresponds to half a second. The adequate relationship then to be measured is then determined according to the maximum peak occurring in the band of n used. This takes into account that the signals of the radar sensors may have a small phase delay or lag between them which may be caused by the movement sequences in the body, or by various transmission delays in the hardware used. The addition in step S34 or in step S44 must be accordingly corrected by this k for each radar sensor.

Figure 3:
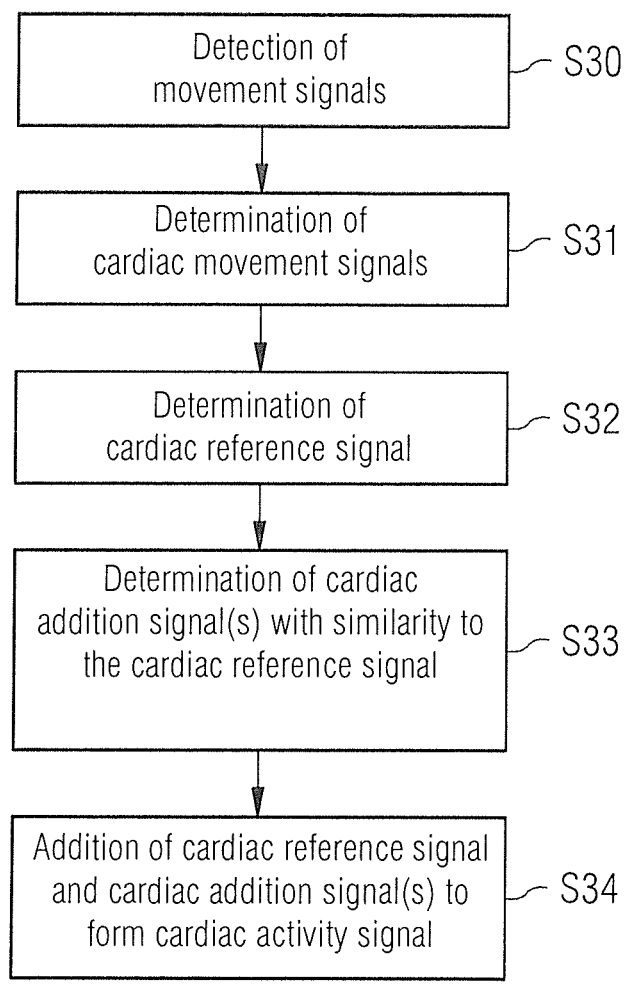
FIG. 3 is a flowchart of the steps which are performed by an evaluation computer of the system from FIG. 2 to determine a cardiac activity signal.
Figure 4:
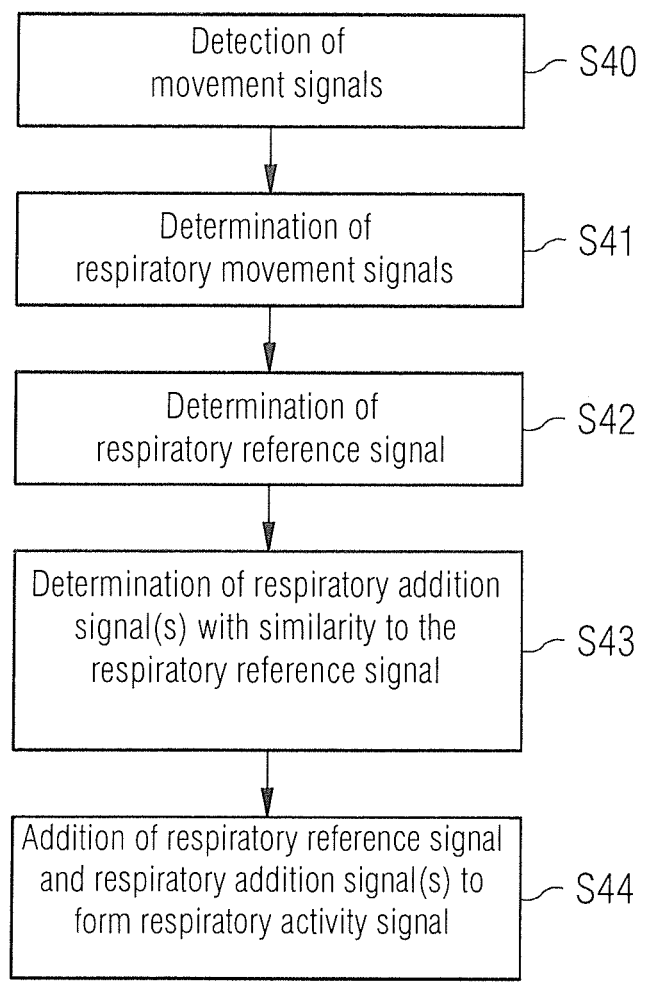
FIG. 4 is a flowchart of the steps to determine a respiratory activity signal.

The processing steps shown with regard to FIGS. 3 and 4 may be performed in an evaluation computer 150 shown in FIG. 2, which has at least one processor 151 and one memory 152. The evaluation computer receives the movement signals via the input-output unit 153, via which it also controls the sensors 110. The evaluation computer 150 can finally transmit the respiratory activity signal 155 and/or the cardiac activity signal 156 to the imaging device 300. The components of the evaluation computer 150 can be designed as hardware components, as software components or as a combination of the two. Both the filters for the generation of the respective addition signals can be provided as separate units, or the associated functions can be performed by the processor unit 151.

Figure 5:
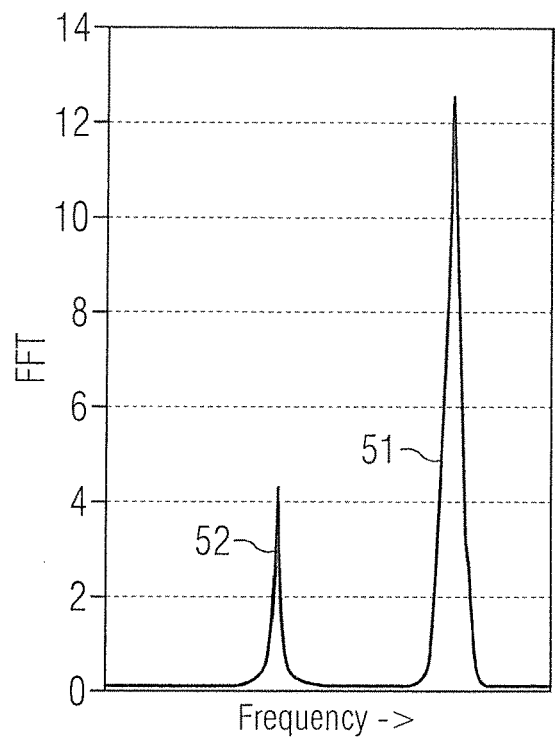
FIG. 5 shows an example of a radar sensor signal in which the signal of the cardiac activity outweighs the respiratory activity.
Figure 6:
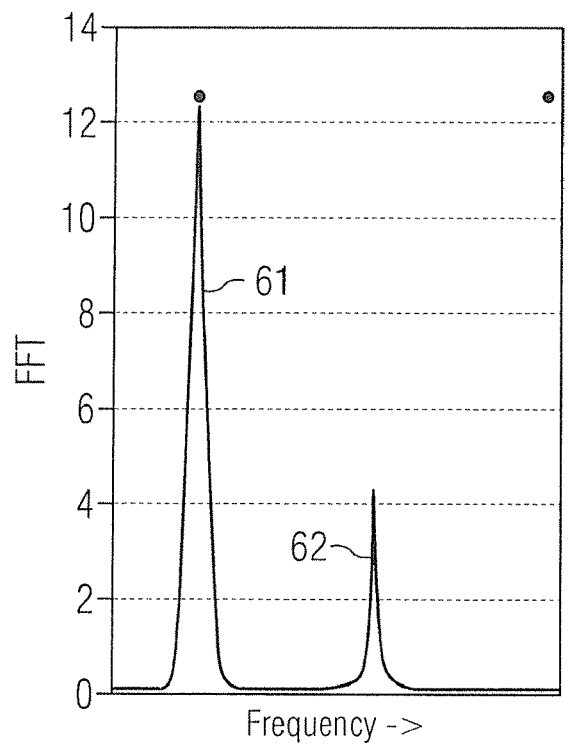
FIG. 6 shows an example of a radar sensor signal in which the respiratory activity outweighs the signal of the cardiac activity.

FIG. 5, for example, shows a radar sensor signal in which the signal of cardiac activity, which has a higher frequency, outweighs the respiratory activity. In selecting the respective sensors, which may provide an addition signal which is sufficiently similar to the respective reference signal, not all the signals need to be assessed by all the sensors of FIG. 2. In the example described, the two reference sensors are located in one of the two subsections 120a, 120b. For example, with sensor signals from the subsection 120b, it is impossible to assess at all whether they create addition signals as it is highly unlikely that a sensor in the subsection 120b still supplies cardiac movement signals with an acceptable signal-to-noise ratio. Furthermore, subgroups 121 or 122 can be created as a function of the position of the respective reference sensor. Subgroup 121 may, for example, create the subgroup of sensors, the signals of which are only or are first assessed for similarity. Subgroup 122 may create the group of sensors in which respiratory addition sensors are sought. In FIG. 5 the amplitude or the peak 51 of cardiac activity is higher than the amplitude or the peak 52. FIG. 6 shows a frequency range of a sensor signal in which the peak of the respiratory signal 61 is higher than the peak 62 of the cardiac signal. The sensor, the signal of which is shown in FIG. 6, could for example be located under the other half of the ribcage but not far from the sternum. FIGS. 5 and 6 also show clearly that in principle the two signals can be separated from one another by appropriate filters such as low pass in relation to band pass or high pass.

The aforementioned processing steps can be performed by the evaluation unit 150 or its processor 151, wherein programs may be found in the storage unit 152 which perform the aforementioned steps during execution by the processor. The system or method described supplies automatic signals for any position of the subject without the attachment of sensors to the subject. These signals describe the cardiac or respiratory movement well and can thus be used to trigger imaging.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for identifying a physiological activity signal of a subject, comprising:
transmitting a plurality of temporal movement signals, respectively acquired by a plurality of movement sensors, from the movement sensors to a computer;
in said computer, analyzing said plurality of temporal movement signals to determine one of said plurality of temporal movement signals that best depicts a physiological movement of the subject that is of interest, and designating said one of said plurality of temporal movement signals as a reference signal for said physiological movement of interest;
in said computer, analyzing temporal movement signals, other than said reference signal, in said plurality of temporal movement signals, according to a reference signal similarity criterion to identify at least one temporal movement signal that is similar to said reference signal, and designating each identified temporal movement signal as an addition signal;
in said computer, using a function result, as said reference signal similarity criterion, that results from the application of a function selected from the group consisting of a cross-correlation function and a cross-covariance function to said reference signal and said temporal movement signals, other than said reference signal, in said plurality of temporal movement signals; and
in said computer, forming a physiological activity signal for said physiological activity of interest by adding said reference signal to each additional signal, and emitting an electronic output from said computer that represents said physiological activity signal.

2. A method as claimed in claim 1 wherein said physiological activity of interest is respiratory movement, and wherein said reference signal is a respiratory reference signal transmitted by a respiratory reference sensor, and wherein said physiological addition signal is a respiratory addition signal.

3. A method as claimed in claim 1 wherein said physiological activity of interest is cardiac movement, and wherein said reference signal is a cardiac reference signal transmitted by a cardiac reference sensor, and wherein said physiological addition signal is a cardiac addition signal.

4. A method as claimed in claim 1 comprising identifying, as a reference sensor, a movement sensor in said plurality of movement sensors, that transmitted said reference signal and designating, as an additional signal sensor, each movement sensor in said plurality of movement sensors that transmitted each identified temporal movement signal and, after designating said reference sensor and each additional signal sensor, deactivating all other movement sensors in said plurality of movement sensors.

5. A method as claimed in claim 1 wherein said physiological movement of interest occurs within a predetermined frequency range and wherein said physiological movement of interest has a characteristic movement attribute associated therewith, and wherein said method comprises determining said one of said plurality of temporal movement signals that best depicts said physiological movement of the subject that is of interest comprises determining one of said plurality of temporal movement signals in which said characteristic movement attribute is highest in said frequency range.

6. A method as claimed in claim 5 wherein said physiological movement of interest is respiration, and wherein said frequency range is a respiratory frequency range and said characteristic movement attribute is signal amplitude.

7. A method as claimed in claim 5 wherein said physiological movement of interest is cardiac motion and wherein said frequency range is a cardiac rate range and wherein said characteristic movement attribute is signal amplitude.

8. A method as claimed in claim 5 comprising filtering each of said temporal movement signals, before said computer, to pass only temporal movement signals to said computer that are within said frequency range.

9. A method for identifying a physiological activity signal of a subject, comprising:
transmitting a plurality of temporal movement signals, respectively acquired by a plurality of movement sensors, from the movement sensors to a computer;

in said computer, analyzing said plurality of temporal movement signals to determine one of said plurality of temporal movement signals that best depicts a first physiological movement of the subject that is of interest, and designating said one of said plurality of temporal movement signals as a first reference signal for said first physiological movement of interest;

in said computer, analyzing temporal movement signals, other than said first reference signal, in said plurality of temporal movement signals, according to a reference signal similarity criterion to identify at least one temporal movement signal that is similar to said first reference signal, and designating each identified temporal movement signal as a first addition signal;

in said computer, forming a first physiological activity signal for said physiological activity of interest by adding said references to each first additional signal, and emitting an electronic output from said computer that represents said first physiological activity signal;

in said computer, also analyzing said plurality of temporal movement signals to determine a further one of said plurality of temporal movement signals that best depicts a second physiological movement of the subject that is also of interest, and designating said further one of said plurality of temporal movement signals as a second reference signal for said second physiological movement of interest;

in said computer, also analyzing temporal movement signals, other than said first and second reference signals, in said plurality of temporal movement signals, according to a second reference signal similarity criterion to identify at least one further temporal movement signal that is similar to said second reference signal, and designating each identified further temporal movement signal as a second addition signal; and in said computer, forming a second physiological activity signal for said second physiological activity of interest by adding said second reference signal to each second additional signal, and emitting an electronic output from said computer that represents said second physiological activity signal.

10. A method as claimed in claim 9 wherein said first physiological activity signal is a respiration signal and said second physiological activity signal is a cardiac signal.

11. A method as claimed in claim 9 wherein said first physiological activity occurs within a first frequency range and said second physiological activity occurs within a second frequency range, and wherein said method comprises filtering said plurality of temporal movement signals, before said computer, to pass only temporal movement signals to said computer in said first frequency range and in said second frequency range.

12. A method as claimed in claim 9 comprising:
in said computer, identifying, as a first reference sensor, a movement sensor in said plurality of movement sensors that transmitted said first reference signal;
in said computer, identifying, as a second reference sensor, a further movement sensor in said plurality of movement sensors that transmitted said second reference signal;
in said computer, dividing said plurality of movement sensors into at least two separate sub-groups and identifying in which of said two separate sub-groups said first reference sensor and said second reference sensor are situated; and
from said computer, if said first reference sensor and said second reference sensor are in a same sub-group, deactivating the movement sensors in all others of said sub-groups.

13. A method for identifying a physiological activity signal of a subject, comprising:
transmitting a plurality of temporal movement signals, respectively acquired by a plurality of movement sensors, from the movement sensors to a computer;
in said computer, analyzing said plurality of temporal movement signals to determine one of said plurality of temporal movement signals that best depicts a physiological movement of the subject that is of interest, and designating said one of said plurality of temporal movement signals as a reference signal for said physiological movement of interest;
in said computer, analyzing temporal movement signals, other than said reference signal, in said plurality of temporal movement signals, according to a reference signal similarity criterion to identify at least one temporal movement signal that is similar to said reference signal, and designating each identified temporal movement signal as an addition signal;
in said computer, identifying, as a reference sensor, a movement sensor in said plurality of movement sensors that transmitted said reference signal;
in said computer, determining said addition signal only from among respective temporal movement signals that were transmitted from respective movement sensors immediately adjacent to said reference sensor; and
in said computer, forming a physiological activity signal for said physiological activity of interest by adding said reference signal to each additional signal, and entitling an electronic output from said computer that represents said physiological activity signal.

14. A system for determining a physiological activity signal in a subject, comprising:
a computer;
a plurality of movement sensors being configured to respectively acquire a plurality of temporal movement signals, and transmit said temporal movement signals from the movement sensors to said computer;
said computer being configured to analyze said plurality of temporal movement signals to determine one of said plurality of temporal movement signals that best depicts a physiological movement of the subject that is of interest, and to designate said one of said plurality of temporal movement signals as a reference signal for said physiological movement of interest;
said computer being configured to analyze temporal movement signals, other than said reference signal, in said plurality of temporal movement signals, according to a reference signal similarity criterion to identify at least one temporal movement signal that is similar to said reference signal, and to designate each identified temporal movement signal as an addition signal;
said computer being configured to identify, as a reference sensor, a movement sensor in said plurality of movement sensors, that transmitted said reference signal and to designate, as an additional signal sensor, each movement sensor in said plurality of movement sensors that transmitted each identified temporal movement signal and, after designating said reference sensor and each additional signal sensor, to deactivate all other movement sensors in said plurality of movement sensors; and said computer being configured to form a physiological activity signal for said physiological activity of interest by adding said reference signal to each additional signal, and to emit an electronic output from said computer that represents said physiological activity signal.

15. A system as claimed in claim 14 wherein each of said movement sensors in said plurality of movement sensors is a radar sensor.

16. A system as claimed in claim 14 wherein said physiological movement of interest occurs within a predetermined frequency range and wherein said physiological movement of interest has a characteristic movement attribute associated therewith, and wherein said computer is configured to determine said one of said plurality of temporal movement signals that best depicts said physiological movement of the subject that is of interest by determining one of said plurality of temporal movement signals in which said characteristic movement attribute is highest in said frequency range.

17. A system as claimed in claim 16 wherein said physiological movement of interest is respiration, and wherein said frequency range is a respiratory frequency range and said characteristic movement attribute is signal amplitude.

18. A system as claimed in claim 16 wherein said physiological movement of interest is cardiac motion and wherein said frequency range is a cardiac rate range and wherein said characteristic movement attribute is signal amplitude.

19. A system as claimed in claim 16 comprising a filter that filters each of said temporal movement signals, before said computer, to pass only temporal movement signals to said computer that are within said frequency range.

20. A system as claimed in claim 14 wherein said computer is configured to use a function result, as said reference signal similarity criterion, that results from the application of a function selected from the group consisting of a cross-correlation function and a cross-covariance function to said reference signal and said temporal movement signals, other than said reference signal, in said plurality of temporal movement signals.

21. A system as claimed in claim 14 wherein said physiological movement of interest is a first physiological movement of interest and wherein said reference signal is a first reference signal for said first physiological movement of interest, and wherein each addition signal is a first addition signal, and wherein said physiological activity signal is a first physiological activity signal, and wherein said method comprises:
  said computer is configured to also analyze said plurality of temporal movement signals to determine a further one of said plurality of temporal movement signals that best depicts a second physiological movement of the subject that is also of interest, and to designate said further one of said plurality of temporal movement signals as a second reference signal for said second physiological movement of interest;
  said computer is configured to also analyze temporal movement signals, other than said first and second reference signals, in said plurality of temporal movement signals, according to a second reference signal similarity criterion to identify at least one further temporal movement signal that is similar to said second reference signal, and to designate each identified further temporal movement signal as a second addition signal; and
  said computer is configured to form a second physiological activity signal for said second physiological activity of interest by adding said second reference signal to each second additional signal, and to emit an electronic output from said computer that represents said second physiological activity signal.

22. A system as claimed in claim 21 wherein said computer is configured to:
  identify, as a first reference sensor, a movement sensor in said plurality of movement sensors that transmitted said first reference signal;
  identify, as a second reference sensor, a further movement sensor in said plurality of movement sensors that transmitted said second reference signal;
  divide said plurality of movement sensors into at least two separate sub-groups and identify in which of said two separate sub-groups said first reference sensor and said second reference sensor are situated; and
  if said first reference sensor and said second reference sensor are in a same sub-group, deactivate the movement sensors in all others of said sub-groups.

23. A system as claimed in claim 21 wherein said computer is configured to:
  identify, as a reference sensor, a movement sensor in said plurality of movement sensors that transmitted said reference signal; and
  determine said addition signal only from among respective temporal movement signals that were transmitted from respective movement sensors immediately adjacent to said reference sensor.

24. A non-transitory, computer-readable data storage medium encoded with programming instructions, said storage medium being loaded into a computer and said programming instructions causing said computer to:
  receive a plurality of temporal movement signals, respectively acquired by a plurality of movement sensors;
  analyze said plurality of temporal movement signals to determine one of said plurality of temporal movement signals that best depicts a physiological movement of the subject that is of interest, and designate said one of said plurality of temporal movement signals as a reference signal for said physiological movement of interest;
  analyze temporal movement signals, other than said reference signal, in said plurality of temporal movement signals, according to a reference signal similarity criterion to identify at least one temporal movement signal that is similar to said reference signal, and designate each identified temporal movement signal as an addition signal;
  use a function result, as said reference signal similarity criterion, that results from the application of a function selected from the group consisting of a cross-correlation function and a cross-covariance function to said reference signal and said temporal movement signals, other than said reference signal, in said plurality of temporal movement signals; and
  form a physiological activity signal for said physiological activity of interest by adding said reference signal to each additional signal, and emit an electronic output from said computer that represents said physiological activity signal.

* * * * *